United States Patent [19]

Ozawa et al.

[11] Patent Number: 4,647,540

[45] Date of Patent: Mar. 3, 1987

[54] AUTOMATIC OBSERVATION SYSTEM FOR MICROORGANISMS AND THE LIKE

[75] Inventors: Tateki Ozawa; Hatsuo Yotsumoto; Tetsu Takeyama, all of Hyogo, Japan

[73] Assignee: Mitsubishi Denki Kabushiki Kaisha, Tokyo, Japan

[21] Appl. No.: 736,892

[22] Filed: May 21, 1985

[30] Foreign Application Priority Data

May 21, 1984 [JP] Japan ................................ 59-100614

[51] Int. Cl.⁴ ...................... C12M 1/34; G02B 27/02; G01N 21/01
[52] U.S. Cl. .................................. 435/291; 435/808; 422/81; 356/246; 356/440; 250/576
[58] Field of Search ............... 435/291, 292, 293, 294, 435/808; 422/81, 82; 356/246, 440; 250/576

[56] References Cited

U.S. PATENT DOCUMENTS

| | | | |
|---|---|---|---|
| 2,649,011 | 8/1953 | Black ................................ | 356/246 |
| 3,459,304 | 8/1969 | Brenchley ...................... | 250/576 X |
| 3,511,573 | 5/1970 | Isreeli ............................... | 422/82 X |
| 3,714,445 | 1/1973 | Blachere et al. ................ | 435/808 X |
| 3,740,156 | 6/1973 | Heigl et al. ..................... | 356/440 X |

FOREIGN PATENT DOCUMENTS 52-89942  7/1977  Japan .
58-188625 12/1983 Japan .

*Primary Examiner*—Margaret A. Focarino
*Attorney, Agent, or Firm*—Sughrue, Mion, Zinn, Macpeak & Seas

[57] ABSTRACT

An automatic observation system for observing objects such as microorganisms contained in a liquid supplied from a container. A sample of the water is fixed between two glass plates, one of which is movable relative to the other by a plunger. A condensor lens is also carried by the plunger. Light from a continuous-output illuminating source is applied through the condensor lens via an optical fiber.

7 Claims, 3 Drawing Figures

AUTOMATIC OBSERVATION SYSTEM FOR MICROORGANISMS AND THE LIKE

BACKGROUND OF THE INVENTION

The present invention relates to an automatic observation system for microorganisms for observing a natural state of microcytes in a liquid, such as germs in sewerage or yeasts during fermentation, by the use of an on-line system.

In general, there are frequent instances where whether treatment is proper or not can readily be determined if the variety, consistency, and the like of microorganisms in a liquid are specified. More specifically, for sewerage treatment by the use of microorganisms, a variety and dominance species of protozoans such as a ciliate, filamentous fungus, or the like, and a bacterium are observed to determine whether the treatment is proper or not.

FIG. 1 shows an observation system applied to a conventional observation apparatus, for example, that disclosed in Japanese Published Patent Application No. 52-89942. In FIG. 1, reference numerals 1, 2, and 3 designate a container wall for containing liquid to be observed, a magnifying optical system, and a cylindrical housing, respectively. The housing 3 has a waterproof-sealed glass 4 at its forward end and receives therein the magnifying optical system 2 through which the liquid in the container can be observed. Reference numerals 5, 6, and 7 respectively denote a television camera, a strobe lamp, and a light guide of bound optical fibers. Reference numerals 8, 9, and 10 indicate an objective lens, a barrel, and an eye lens, respectively, which constitute the magnifying optical system. Reference numerals 11, 12, and 13 denote a control circuit, a strobe power source, and a television monitor. Reference numerals 14, 15 and 16 indicate an image memory, a signal processing circuit, and an indicator.

The strobe lamp 6 emits pulses of light when the strobe power source 12 is so instructed by the control circuit 11. Upon the generation of each pulse of light, the television camera 5 effects a scanning operation in response to a scanning start signal from the control circuit 11. The area around a focal point f in the liquid is magnified and projected by the magnifying optical system 2 onto an image pickup surface of the television camera 5. The magnified projected image is thereby converted as an image information video signal.

The video signal is inputted to either the television monitor 13 or the picture memory 14 as selected by changeover switches $S_1$ and $S_2$. When the video signal is inputted directly to the television monitor 13, the image which is obtained when the strobe lamp 6 emits light is projected onto the screen of the television monitor 13. The resulting video signal is received by the image memory 14 to be processed with the signal processing circuit 15, thereby to display the processed image on the screen of the television monitor 13. The duration of the light pulses emitted by the strobe lamp 6 is suitably adjusted according to magnification of the magnifying optical system 2 and the flow rate of liquid.

In the conventional automatic observation system arranged as described above, microcyclic motion of the microorganisms is made to appear stationary by the flashes emitted by the strobe lamp 6. This results in disadvantages, however, in that a control circuit must be employed to define the timing between the initiation of light emission of the strobe lamp 6 and the scanning of the television camera 5, and the image memory 14 and the signal processing circuit 15 must be provided for a good quality image.

The conventional automatic observation system also requires complicated maintenance and inspection since slime or the like can collect on the forward end 7a of the light guide and the surface of the glass 4.

Moreover, the overall structure of the apparatus limits its installation to the peripheral wall of the container for the liquid to be observed.

SUMMARY OF THE INVENTION

The present invention has been made in view of the drawbacks discussed above. A specific object of the invention is the provision of an automatic observation system for microorganisms which is capable of providing an image of better quality under continuous illumination (as in a microscope) and of providing automatic flushing to simplify maintenance and inspection. It is a further object of the invention to provide such an automatic observation system which can be installed at any desired location.

The aforementioned and other objects of the invention are met by an automatic observation system for microorganisms comprising means for observing a liquid including means for fixing a sample portion of liquid to be observed, means for conducting liquid in a container to the observation means, and means for washing the fixing and the conducting means.

DESCRIPTION OF THE PREFERRED EMBODIMENTS

Figure 1:
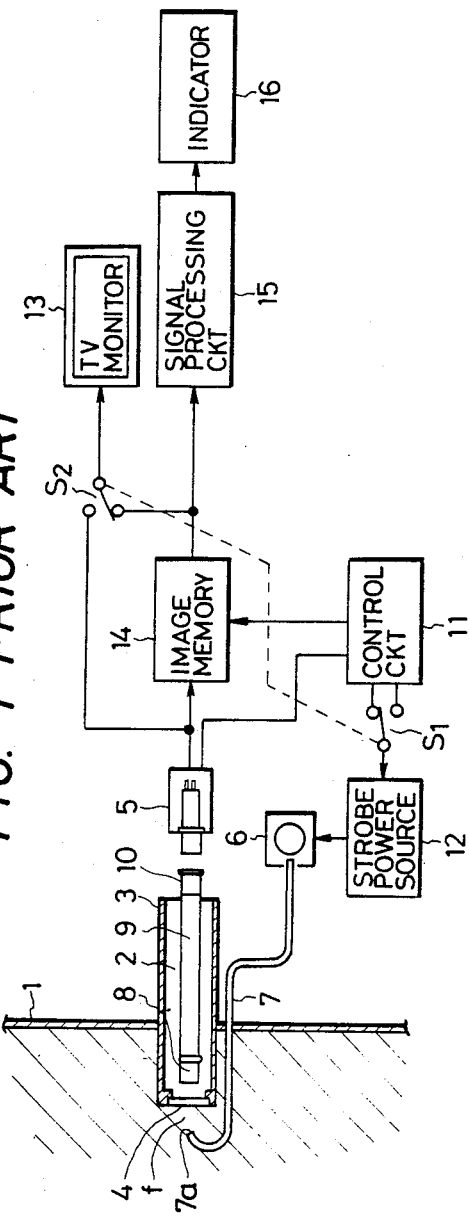
FIG. 1 is a block diagram showing a conventional observation apparatus for microcytes in a liquid.
Figure 2:
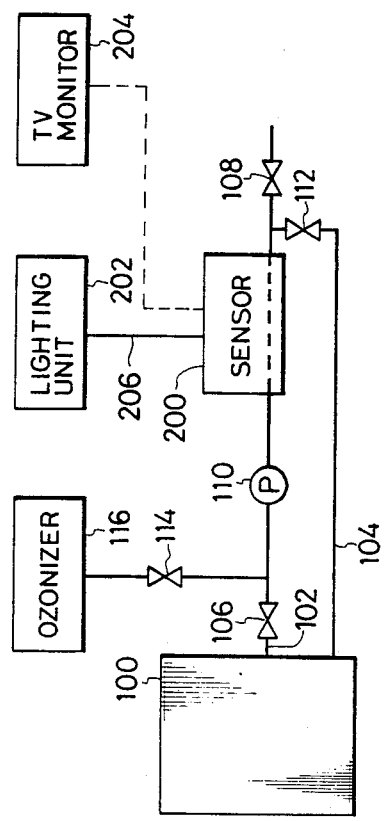
FIG. 2 is a block diagram of a preferred embodiment of an automatic microorganism observation system according to the present invention.

The invention will be explained in detail in conjunction with FIGS. 2 and 3 of the accompanying drawings showing an automatic observation system of the invention. FIG. 2 shows schematically the overall contruction of the inventive automatic observation system.

As shown in FIG. 2, water or other liquid to be observed and which contains therein microorganisms is entrapped in a container 100 for liquid observation. Pipes 102 and 104 are coupled to each other in the container 100. The pipe 102 is provided with valves 106 and 108 and a pump 110. The other pipe 104 is provided with a valve 112 by which the pipe lines 102 and 104 can be coupled to each other.

An ozonizer 116 is connected by a valve 114 between the valve 106 for the pipe 102 and the pump 110. A sensor 200 is disposed between the pump 100 for the pipe line 102 and the valve 108. A lighting unit 202 and a television monitor 204 are coupled to the sensor 200.

The ozonizer 116 serves to sterilize and clean the interior of the pipes and the liquid passage through the sensor.

Figure 3:
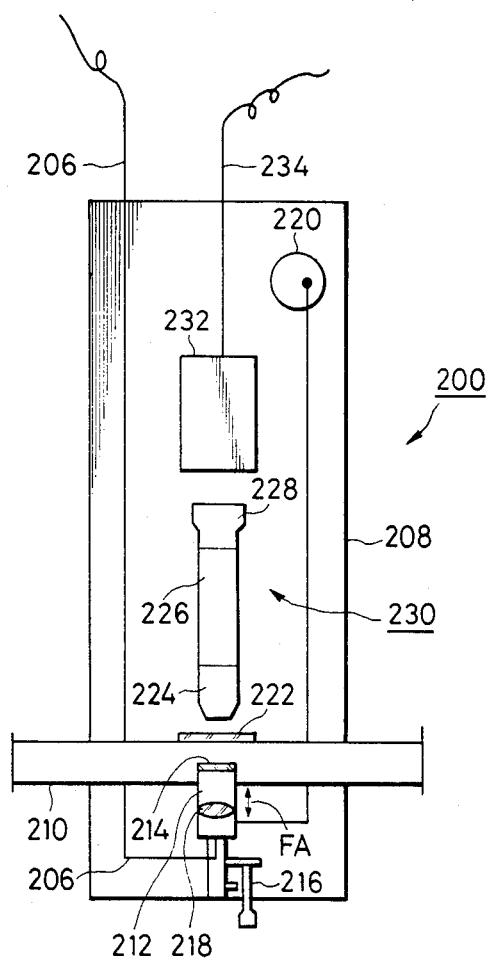
FIG. 3 is a side view of a sensor used in the system of FIG. 3.

The sensor 200, as shown, in FIG. 3, includes an enlarging optical system, a television camera, and a fixing mechanism for the microorganisms, which components are mounted together as a unit. The lighting unit 202 outputs continuous light, which is conducted by an optical fiber 206 to the sensor 200. The pump 110 pumps the liquid to be observed. The valves 106, 108, 112 and 114 may be electromagnetic, moto-driven, or air-driven types.

Next, the sensor 200 will be described in more detail with reference to FIG. 3. As shown in that drawing, a sensor body 208 is provided downwardly thereof with a liquid passage 210 coupled to the pipe 102. A transparent glass 214, mounted in substantially the central position of the liquid passage 210, is vertically movable by a plunger 212, as indicated by an arrow FA. Vertical movement of the transparent glass 214 is limited by a stop 216. A condensor lens 218 is positioned in the plunger 212 below the transparent glass 214. The optical fiber 206 extends downwardly of the condensor lens 218. More specifically, light from the lighting unit 202 passes through the optical fiber 206 and the condensor lens 218 to the transparent glass 214, which is thus illuminated from below. The plunger 212 is driven by a drive motor 220.

Another transparent glass 222 is located in the wall of the liquid passage 210, centrally thereof, and opposite the transparent glass 214. A magnifying optical system 230 consisting of an objective lens 224, a barrel 226, an an eyepiece lens 228 is disposed upwardly of the transparent glass 222. A television camera 232, positioned upwardly of the magnifying optical system 230, receives the image under the transparent glass 212 via the magnifying optical system 230. The television camera 232 is connected by a cable 234 to the television monitor 204.

The operation of this automatic observation system will now be explained with reference to a case where microcytes are to be observed.

At first, the valves 106 and 112 are opened and the other valves 108 and 114 are closed. Thus, a closed loop is formed with connects the container 100 to the sensor 200. The pump 110 is then driven to pump the liquid from the container 100 into the sensor 200. The liquid to be observed circulates through the closed loop.

At this time, the plunger 212 is driven by the drive motor 220 to move the transparent glass 214 upwardly, thereby fixing a sample of the liquid between the transparent glasses 214 and 222. The distance between the transparent glasses 214 and 222 is suitably determined by the plunger 212 and the stop 216 as to correspond to the size of the microorganism or other object to be observed.

Light is then outputted from the lighting unit 202 to illuminate the fixed liquid. The image of the microorganisms in the liquid to be observed is enlarged by the magnifying optical system 230 and picked up by the video camera 232. In other words, the enlarged image of the microorganisms contained in the fixed liquid is converted by the video camera 232 to a video signal, which is applied into the television monitor 204.

Cleaning operations performed after completion of the aforementioned observation operations will now be described.

Initially, the valves 106 and 112 are closed and the valves 108 and 114 are opened. Ozone-containing water generated by the ozonizer 116 or a liquid mixture of ozone-containing water and an ozone-containing gas is flushed into the pipe 102. This is carred out by the pump 110 with the ozone-containing water passing through the liquid passage 210 in the sensor 200 and being discharged from the valve 108 to the outside. The aforementioned operation effects washing of the pipe 102 and the liquid passage 210. This flushing is performed preferably one or more times a day, typically for one or more minutes each time, depending on the consistency or flow rate of the ozone-containing water.

When observation is to be resumed after the washing operation, the valve 114 is closed whereas the valve 106 is opened. The pump 110 is then run until the ozone-containing water in the pipe 102 and the liquid passage 210 is replaced with the liquid to be observed. After discharge of the residual ozone-containing water, the valve 112 is opened and the valve 108 is closed, forming a closed loop through which the liquid circulates. Subsequent observation operations can then be performed as described above. If desired, the aforementioned observation and washing operations can be automatically carried out by a control device.

It is noted that the invention is not limited to the aforementioned embodiment. Specifically, it is possible to employ liquid cleansers other than ozone-containing water, such as hypochlorite, chlorine, hydrogen peroxide water, and the like, or a synthetic cleanser. Washing conditions may be suitably selected according to a type and consistency of the cleanser. Mechanical washing devices such as a brush, wiper, or the like may be employed instead of a liquid cleanser. Moreover, although a motor is used as a drive source of the plunger, other sources such as air-driven or electromagnetic force-driven sources may be employed.

As set forth hereinbefore, according to the inventive automatic observation system for microorganisms and the like, because the liquid to be observed is fixed for observation, an image of better quality is obtained by continuous illumination. Also, because the liquid to be observed is fed from the container to the sensor in the outside, maintenance operations such as cleaning may be simplified. Further, there is no limitation as to the location where the system can be installed.

We claim:

1. An automatic observation system for microorganisms and the like adapted to automatically display on indicator means the microorganisms and the like contained in water from a container, wherein the improvement comprises: means for observing samples of said water including means for fixing a sample of said water; means for conducting water to be observed from said container to said observation means; indicator means for automatically observing said samples; means for continuously illuminating said water sample as fixed; and means for washing said fixing means with fluid other than sample water and said conducting means.

2. The automatic observation system as set forth in claim 1, wherein said observing means comprises means for enlarging an image projected by said illuminating means, and image pickup means for converting said enlarged image to an electrical signal, said enlarging means and said image pickup means being integrally formed with said fixing means.

3. The automatic observation system as set forth in claim 1, wherein said washing means comprises means for washing with a liquid cleanser selected from the group consisting of ozone-containing water, hypochlorite, chlorine, and hydrogen peroxide water.

4. The automatic observation system as set forth in claim 1, wherein said washing means comprises means for washing with a synthetic cleanser.

5. The automatic observation system as set forth in claim 2, wherein said fixing means comprises first and second transparent glass plates disposed opposite to and parallel to each other, and a plunger for selectively moving said first glass plate in a direction perpendicular to said second glass plate.

6. The automatic observation system as set forth in claim 5, wherein said fixing means further comprises a condensor lens carried by said plunger, and an optical fiber for conveying light from said illuminating means to a side of said condensor lens opposite said first glass plate.

7. An automatic observation system for microorganisms and the like adapted to automatically display on indicator means the microorganisms and the like contained in water from a container, wherein the improvement comprises: means for observing samples of said water including means for fixing a sample of said water; means for conducting water to be observed from said container to said observation means; indicator means for automatically observing said samples; means for continuously illuminating said water sample as fixed; means for enlarging an image projected by said illuminating means; image pickup means for converting said enlarged image to an electrical signal, said enlarging means and said image pickup means being integrally formed with said fixing means; and means for washing said fixing means with fluid other than sample water and said conducting means, wherein said fixing means comprises first and second transparent glass plates disposed opposite to and parallel to each other, a plunger for selectively moving said first glass plate in a direction perpendicular to said second glass plate, a condenser lens carried by said plunger, and an optical fiber for conveying light from said illuminating means to a side of said condensor lens opposite said first glass plate.

* * * * *